United States Patent [19]

Kelman

[11] Patent Number: 4,648,878
[45] Date of Patent: Mar. 10, 1987

[54] POSTERIOR CHAMBER LENS IMPLANT

[76] Inventor: Charles D. Kelman, 269 Grand Central Pkwy., Bldg. 3, Floral Park, N.Y. 11005

[21] Appl. No.: 812,256

[22] Filed: Dec. 23, 1985

[51] Int. Cl.⁴ .............................................. A61F 2/16
[52] U.S. Cl. ........................................................ 623/6
[58] Field of Search ............................................ 623/6

[56] References Cited

U.S. PATENT DOCUMENTS

| | | | |
|---|---|---|---|
| 4,253,200 | 3/1981 | Kelman | 623/6 |
| 4,418,431 | 12/1983 | Feaster | 623/6 |
| 4,581,031 | 4/1986 | Koziol et al. | 623/6 |

Primary Examiner—Ronald L. Frinks
Attorney, Agent, or Firm—Henry Sternberg

[57] ABSTRACT

A posterior chamber lens implant for use after extra-capsular surgery, i.e. surgery in which the rear membrane of the lens or posterior capsule is left intact. The lens implant comprises an optic having a front surface and a rear surface and the implant is secured within the posterior chamber of the eye. In one form of the invention, a pair of position-fixation means are adapted to support the optic in the posterior capsule of the eye with the planar rear face of the optic inclined with respect to the posterior capsule, with the superior rear edge of the optic in contact with the posterior capsule and the inferior rear edge spaced from the posterior capsule. While in a second form of the invention, the position-fixation means are such that they press the superior peripheral rear edge of the optic against the posterior capsule for deforming the latter in a manner to space the posterior capsule away from the mid-portion of the rear face of the optic. In a third form of the invention, the optic is conventionally held in conventional position in the posterior capsule, but the optic itself is formed with a prism-shaped portion at the rear thereof. The prism-shaped portion defines a rear planar surface which is inclined with respect to the posterior capsule upon conventional implantation. The implant of the present invention thus facilitates laser posterior capsulotomy in the event of clouding of the posterior capsule following extra-capsular surgery.

14 Claims, 7 Drawing Figures

POSTERIOR CHAMBER LENS IMPLANT

BACKGROUND OF THE INVENTION

The present invention relates to a posterior chamber lens implant for use after extra-capsular cataract surgery.

In extra-capsular surgery, a surgical opening is formed through the front membrane or anterior capsule of the lens of the human eye and the cataracted lens is surgically removed. During such surgery, however, it is important to leave the posterior capsule of the lens intact so that it forms a barrier between the vitreous humor and the aqueous humor.

Following the removal of the cataract it is often desirable to replace the human lens with an artificial lens implant in order to restore sight to the eye. It has been found that posterior chamber lens implants are considered by some surgeons to be medically superior to anterior chamber and pupil lens implants.

In such posterior chamber lens implants, the optic is typically secured in place in the posterior chamber by loops or haptics extending outwardly from the optic and seating either in the cul-de-sac of the anterior and posterior capsule or in ciliary sulcus of the eye.

In a high incidence of cases, after a period of time following implantation of the lens, the posterior capsule becomes clouded and obscures vision. In order to restore the vision to the eye after this has occurred, it is necessary to perform a posterior capsulotomy to remove the portion of the posterior capsule that is behind the optic.

Recently it has become popular to use laser posterior capsulotomy in which a laser is focused on the posterior capsule through the pupil. Upon activation of the laser, the laser causes an opening through the posterior capsule behind the optic to be made, thus, restoring vision to the eye.

At present, however, laser posterior capsulotomies can be safely performed only with specially configurated lenses which, however, exhibit some disadvantageous optical characteristics as a result of their special configurations. It must be remembered, in this connection, that the conventional posterior chamber lens is implanted with its flat rear face in contact with the posterior capsule. Consequently, there is a substantial risk of damaging the optic while performing laser capsulotomy on the membrane of the eye which is in contact with the rear face of the optic. One lens which has been designed specifically for laser capsulotomy, but which has some of the optical disadvantages alluded to above, is the lens described in my own U.S. Pat. No. 4,495,665. While the rearward projections of a lens according to my said patent provide adequate spacing of the posterior capsule from the mid-portion of the rear face of the optic, nevertheless, because of their location in the path of light being transmitted through the optic to the retina of the eye, the projections, according to my patent, tend to reduce the effective size of the optic for light transmissibility and may interfere in some other ways, for example, slight distortions of the vision of the eye.

Another known posterior chamber lens capable of spacing portions of the rear face of an optic from the posterior capsule is the lens described in the patent to Hoffer U.S. Pat. No. Re. 31,626. That patent discloses an annular lip projecting rearwardly from the rear face of the optic for providing the desired spacing. This construction suffers from the very same infirmities, even more exaggerated, which I have just described with respect to my own patent. Thus, the Hoffer annular lip tends to substantially reduce the effective size of the optic since it also is interposed in the region through which light is transmitted through the optic to the retina, resulting furthermore in the possibility of substantial distortion in the vision of the eye. A still further known posterior chamber lens capable of spacing portions of the rear surface of an optic from the posterior capsule is the lens described in the patent to Myers U.S. Pat. No. Re. 31,998. That patent discloses an optic having a concave rear surface as a result of which the central portion of such rear surface is spaced from the posterior capsule when the surrounding annular peripheral portion of the optic is in contact with the posterior capsule. The optics according to this construction are, however, very difficult and costly to make free of optical distortion. Since the distortion introduced by the rear concave surface must be compensated for very accurately by the convex anterior surface.

SUMMARY OF THE PRESENT INVENTION

The present invention provides a posterior chamber lens implant which enables a subsequent laser posterior capsulotomy to be performed without interposing additional elements within the optical field which elements are of such a nature as to reduce the effective size of the optic and/or cause distortions which cannot be readily compensated for by a change in the configuration of the anterior surface of the optic.

In brief, the lens implant of the present invention comprises an optic having a generally convex front surface, a generally planar rear surface and means for securing the optic such that it is positioned and centered within the posterior chamber. Preferably, the securing means comprises one or more haptics which are seated in the superior and inferior peripheral portions of the posterior capsule between the anterior and posterior walls thereof.

Unlike the previously known posterior chamber lens implants, however, the present invention comprises means for spacing the mid-portion of the rear surface of the optic forwardly of the posterior capsule, thus forming a space between such mid-portion of the rear surface of the optic and the posterior capsule, without reducing the effective optical size of the optic and without introducing any substantial optical distortions. According to a preferred form of this invention the position-fixation means comprise a pair of haptics extending generally radially outwardly from opposite peripheral portions of the optic. The haptics are configured to extend outwardly of the optic at different angles with respect to the plane of the rear face of the optic. The angles at which the haptics extend are chosen such that one of the haptics, e.g. the haptic which will be located in superior position on implantation of the lens, will always be inclined at a substantially greater positive angle to the rear face of the optic than the opposite, i.e. inferiorly positioned haptic. In the preferred form of the invention, one peripheral portion of the rear face of the optic is pressed by the haptics against the posterior capsule so as to deform the latter and as a result of such deformation cause a space to be created between the posterior capsule and the mid-portion of the rear face of the optic. Consequently, in such preferred lens, the superior haptic is positioned at such an angle of inclination with respect to the rear face of the optic that, following implantation of such lens into the posterior chamber, the superior haptic will exert sufficient pressure on the optic to press the superior rear edge of the rear surface of the optic against the posterior capsule for deforming the latter in the manner described above.

In a second preferred embodiment of the invention, the haptics are configurated such that they will position the optic in the posterior chamber with the superiorly positioned peripheral portion of the rear edge of the optic contacting the posterior capsule and the rear edge of the inferiorly located peripheral portion of the rear face of the optic spaced from the posterior capsule a distance sufficient to result in a spacing of the mid-portion of the rear face of the optic from the posterior capsule a distance sufficient to allow for safe laser capsulotomy. Thus, according to this embodiment, only the rear edge of the superior peripheral portion of the optic abuts against the posterior capsule. The remainder of the rear surface of the optic is inclined forwardly away from the posterior capsule.

In a third preferred embodiment of the invention, the optic is formed with a prism-shaped posterior portion located behind the convex anterior portion of the optic. The prism-shaped portion defines a rear planar surface which is inclined with respect to the optical axis of the anterior optical portion. The lens in accordance with this third embodiment is implanted with the use of conventional haptics conventionally positioned and achieves the desired result by having a naturally inclined rear surface. The superior peripheral portion of the inclined rear face abuts the posterior capsule, while the inferior opposite peripheral portion of the rear face is spaced from the posterior capsule.

In practice, only a relatively small spacing, for example, 0.1 mm, is necessary between the mid-portion of the rear face of the optic and the posterior capsule in order to enable a laser posterior capsulotomy to be safely performed. Nevertheless, a spacing of 0.2 mm to 0.5 mm is preferred. Since laser posterior capsulotomies are typically performed in the region of the optical axis of the eye, with particular emphasis to extending the capsulotomy inferiorly of the optical axis of the eye to provide for reading vision, the optic according to the present invention, has its rear face inclined away from the posterior capsule in such region, i.e. below the optical axis.

In accordance with the invention a posterior chamber intraocular lens intended for implantation in a human eye after extra-capsular cataract extraction, comprises a substantially rigid optic, a curved front surface, a continuous substantially planar rear face having a pair of opposed peripheral portions each having an outer edge. The rear surface has a mid-portion between the pair of peripheral portions and the a lens further includes a means for securing the optic to the eye such that the planar rear face is inclined with respect to the posterior capsule. The outer edge of one of the peripheral portions is in contact with the posterior capsule and the outer edge of the other of the peripheral portions is spaced from the posterior capsule. The inclination is such that the mid-portion is spaced from the posterior capsule by a distance sufficient to safely allow a subsequent laser posterior capsulotomy.

The posterior chamber intraocular lens according to the invention includes a first position-fixation means connected to the optic in the region of one of the pair of peripheral portions and second position-fixation means connected to the optic in the region of the other of the pair of peripheral portions. The first position-fixation means and the second position-fixation means cooperate with the optic for positioning the outer rear edge of one peripheral portion in contact with the posterior capsule and for positioning the outer rear edge of the other peripheral portion at a location spaced from the posterior capsule.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF PREFERRED EMBODIMENTS OF THE PRESENT INVENTION

Figure 1:
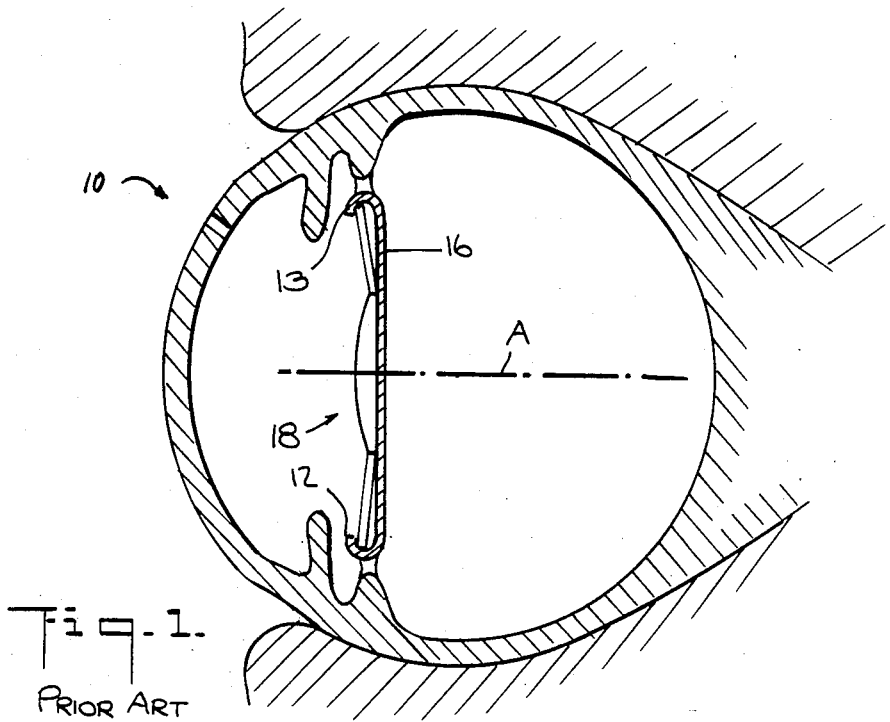
FIG. 1 is a fragmentary sectional view illustrating a conventional lens implant, according to the prior art, in the posterior chamber of an eye.
Figure 2:
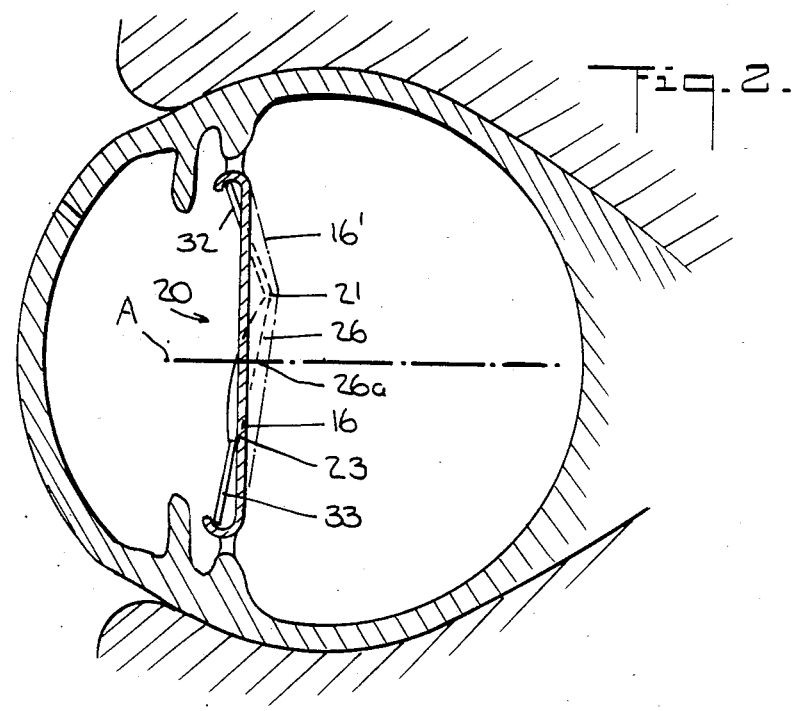
FIG. 2 is an enlarged fragmentary sectional view illustrating a first preferred embodiment of the lens implant of the present invention within the posterior chamber.

With reference first to FIGS. 1 and 2, a human eye 10 is shown following extra-capsular surgery. During extra-capsular surgery, an opening 12 is formed in the anterior capsule 13 for removal of the cataract. In doing so, the posterior capsule 16 is left intact as well as a generally annular peripheral portion of the anterior capsule 13.

A conventional posterior chamber lens 18 of the type known in the prior art, is shown implanted in the posterior capsule of the eye with the haptics thereof positioned in the cul-de-sac between the posterior capsule 16 and the remaining annular portion of the anterior capsule 13 as is well known in the art. In accordance with the prior art the flat rear surface of the optic, or medial light focusing lens body of the lens 18 is generally coplanar with and typically lies flat against the anterior surface of the posterior capsule 16. At the time of implantation of a posterior chamber lens the posterior capsule may sometimes be dish-shaped, i.e. slightly concave, and may have a somewhat irregular, i.e. wavy, surface. Shortly after extra-capsular surgery, however, the posterior capsule becomes relatively taut and flat as a result of fibrosis. The posterior capsule 16, therefore, soon after such surgery assumes the shape shown in FIG. 1. According to a first preferred embodiment of the posterior chamber lens, an implant 20 according to the present invention, comprises a central optic or medial light focusing lens body 22 having a front convex surface 24 and a generally plannar continuous rear face 26. The optic 22, which is typically constructed of a plastic such as polymethylmethacrylate is designed to reproduce or approximate the optical qualities of the natural lens of the human eye. According to the present invention, the optic, or lens body 22, is constructed such that it will be generally rigid and able to resist the forces exerted thereon during and after implantation in the eye without distortion of the generally planar characteristics of the rear face of the optic.

Figure 3:
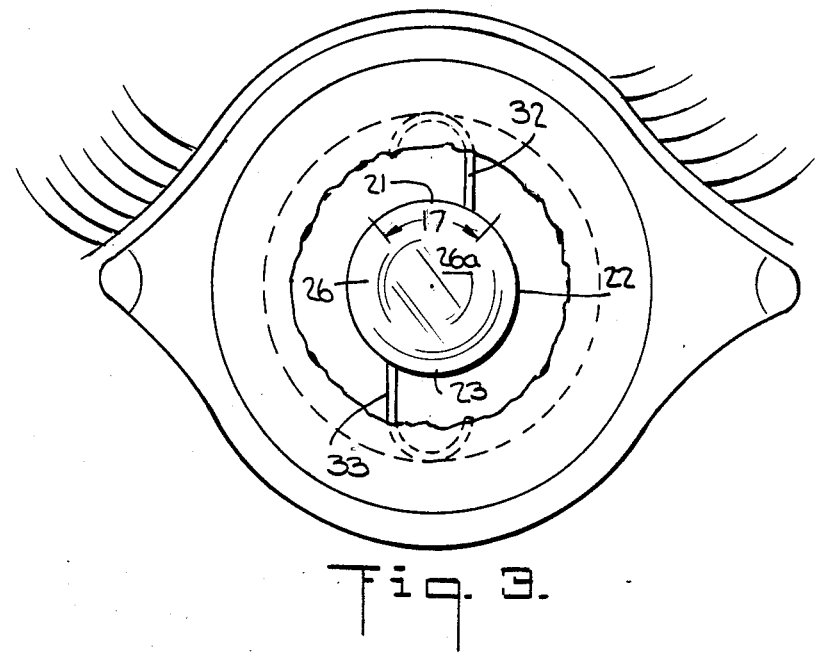
FIG. 3 is a front elevational view of a lens according to FIG. 2.

As best shown in FIG. 3 the generally planar rear surface of the optic rear face 26 has a pair of opposed peripheral portions 21 and 23. When the lens is implanted, peripheral portion 21 will be located superiorly while diametrically opposed peripheral portion 23 will be located inferiorly.

The optic is secured within the eye by the use of securing means preferably in the form of haptics 32 and 33. The haptics 32 and 33 are generally J-shaped as is well known in the art. Also, the haptics 32 and 33 may be unitary with the optic 22 but preferably are formed of polypropelene and integrally connected with the optic 22 by any of several connecting means well known in the prior art.

The present invention is directed to a lens in which the planar rear face of the optic is inclined with respect to the posterior capsule, after implantation of the lens in an eye such that one peripheral portion thereof is in contact with the posterior capsule for positive positioning and another portion thereof is spaced from the posterior capsule. The direction of the inclination is such that the superior peripheral portion 21 of the rear face 26 is in contact with the posterior capsule 16, while the inferior peripheral portion 23 is out of contact with the posterior capsule by such an amount that a mid-portion 26a, i.e. a portion in the region of the optical axis "A" of the eye, is spaced from the posterior capsule by a distance sufficient to safely allow a subsequent laser posterior capsulotomy. The novel results of the present invention may be accomplished by any one of several different constructions as will now be explained.

It will be seen from FIG. 1 that the prior art lenses are typically constructed with their haptics inclined outwardly and forwardly, i.e. in anterior direction, with respect to the lens body, by an angle which is typically approximately 4° with respect to the rear planar face of the optic. This serves both to more positively seat the optic against the posterior capsule and also to reduce the risk of contact between the optic and the iris. Unfortunately, this does not provide for a laser space behind the lens which will safely permit subsequent laser posterior capsulotomy.

Figures 4, 5, 6, 7:
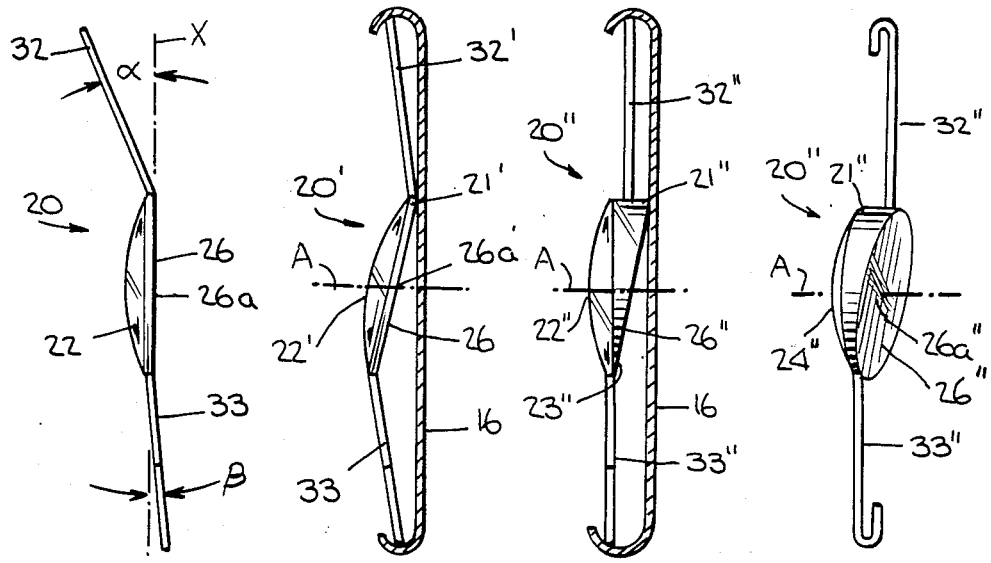
FIG. 4 is a schematic side view illustrating the lens according to FIGS. 2 and 3.
FIG. 5 is an enlarged fragmentary sectional view illustrating a second preferred embodiment of the lens implant of the present invention within the posterior chamber.
FIG. 6 is an enlarged fragmentary sectional view of a third embodiment of the lens implant of the present invention within the posterior chamber.
FIG. 7 is a perspective view of the lens according to FIG. 6 showing the rear face of the optic.

According to the preferred embodiment of the present invention shown in FIGS. 2 and 4, the superior and inferior haptics 32, 33 are not only each connected to the optic 22 at a different angle with respect to the rear face but the angle of inclination $\alpha$ between the superior haptic 32 and the plane of the rear face 26 of the lens body is substantially greater than the angle $\beta$ between the inferior haptic 33 and the same plane of the rear face of the lens body. By way of example, a satisfactory lens in accordance with this embodiment of the present invention has a superior haptic 32 making an angle alpha of approximately 16° with respect to the rear face of the lens body while the inferior haptic 33 makes an angle beta of 0°, i.e. is parallel to the rear face 26 of the lens body. It will be seen that a lens in accordance with this construction, when it is implanted in the posterior capsule, as shown in FIG. 2, will have its lens body or optic 22 tilted with respect to the generally planar surface of the posterior capsule 16, to such an extent that the rear edge of the superior peripheral portion 21 will be pressed against the posterior capsule, depressing the latter rearwardly. Consequently, the posterior capsule will be deformed generally into the shape shown in dashed lines at 16' in FIG. 1. It must be remembered, in this connection, that as a result of fibrosis, the posterior capsule assumes characteristics which resemble the characteristics of Saran Wrap, i.e. it becomes relatively taut so that pressure against it by the superior rear edge, along about the upper 90° arc 17 of the rear edge, results in movement of the remainder of the posterior capsule away from the rear face 26 of the lens body into the dashed position 16' shown in FIG. 2. Consequently, the remaining portions of the optic 22, including the mid-portion 26a of the rear face, are spaced from the posterior capsule. This spacing, which is exaggerated in FIG. 2, for clarity, is preferably between about 0.10 mm and 0.5 mm in the region of the optical axis "A". When a lens according to this construction is implanted in the eye, the rear face of the optic 22 is tilted such that its inferior peripheral portion 23 is inclined forwardly approximately 4° with respect to the plane of the posterior capsule.

With reference now particularly to FIG. 5, a further preferred embodiment 20' of the lens implant is there shown and comprises an optic 22' which is idential to optic 22. The difference between the embodiment shown in FIG. 5 and that shown in FIGS. 2 and 3 is that the means for securing the optic to the eye are different. Thus, in the embodiment of FIG. 5 the superior haptic 32' is inclined at an angle of approximately 8° with respect to the planar rear face 26' of the optic while the inferior haptic 33 is inclined negatively, i.e. inclined in posterior direction, also by an angle of about 8°. Thus, the superior haptic is inclined about 8° in anterior direction, while the inferior haptic is inclined about 8° in posterior direction. Consequently, the optic 22', when it is secured in the eye will assume the position shown in FIG. 5 wherein the upper peripheral portion 21' of the planar rear face thereof is closely adjacent to and preferably in contact with, the posterior capsule 16, while the lower peripheral portion 23' is spaced from the posterior capsule 16, thus creating sufficient spacing in the region of the optical axis, i.e. between the mid-portion 26a' of the rear face of the optic and the posterior capsule 16, for safe laser capsulotomy. With the aforesaid angular relationships for the haptics the optic 22' would be inclined at an angle of about 4° with the posterior capsule and the resulting spacing of the mid-portion 26a' from the posterior capsule would be approximately 0.250 mm, while in accordance with the FIG. 2 embodiment above, the corresponding spacing would be approximately 0.125 mm. Both the spacing and the angle of inclination are shown exaggerated in the drawing for the sake of clarity. Any space in excess of 0.1 mm is believed sufficient for safely carrying out a posterior laser capsulotomy.

Of course, it will be seen that by varying the angles of inclination of the haptics, provided that one of the haptics, for example, the superior haptic 32 is always at a greater positive angle of inclination with respect to the rear face of the optic, than the inferior haptic, various amounts of spacing between the mid-portion of the rear face and the posterior capsule may be achieved. Care should be taken, however, not to allow the inferior peripheral portion of the optic to extend more than 2-3 mm anteriorly of the posterior capsule in order to avoid the risk of contact between the optic and the iris.

With reference now particularly to FIGS. 6 and 7, a still further preferred embodiment 20" of the lens implant is there shown and comprises an optic 22" which has a shape which may best be described as a conventional posterior chamber lens having a prism-shaped portion at the rear thereof. Thus, instead of having a flat rear surface generally at right angles with respect to the optical axis, the lens implant 20" has an inclined rear surface 26", inclined with respect to the optical axis "A", at an angle between about 70° and 86° with resepct to axis "A". According to this embodiment, the haptics 32" and 33" may be of the conventional type and exhibit the conventional 4° angle of inclination with respect to a vertical plane. Consequently, by maintaining the optic in conventional orientation, the inclined rear face 26" of the optic 22" will be inclined with respect to the posterior capsule at the angle of inclination designed into the prism, thus, creating a space in the region of the mid-portion 26a" of the rear face of the optic, sufficient for safe laser capsulotomy. According to this embodiment also, the upper peripheral rear edge 21" abuts against the posterior capsule 16 and the mid-portion 26a" of the optic rear surface is spaced forwardly from the posterior capsule.

By inclining the rear face of the optic so that the mid-portion is sufficiently spaced from the posterior capsule, the present invention enables the safe use of a laser to perform a posterior capsulotomy in the event that the posterior capsule subsequently becomes clouded or obscured. As previously described, unlike the prior art lenses in which additional projections in the form of an annular ring or other surface discontinuities were located at the rear surface of the optic, the present invention is able to achieve a spacing of the mid-portion of the rear surface from the posterior capsule, i.e. the region where laser capsulotomies are typically performed, without reducing the effective size of the optic and without any disturbing interferance with the transmission of light therethrough. It has been found that an angle of inclination of a posterior chamber lens of as much as 15° results only in 1.0 diopter of astigmatism, while an inclination of the rear face of an optic with respect to the posterior capsule of about 20° results only in about 1.5 diopters of astigmatism. It is interesting to note that in conventional lens implant procedures many of the patients have, as an inherent result of the implant, approximately 1.0 diopter of astigmatism. Therefore, it may be possible to use the astigmatism resulting from the inclination of the optic in accordance with the present invention to counterbalance some, or all, of the astigmatism found to be inherently resulting from implantation of a lens, so that no further adjustment will be required. On the other hand, in those instances where further optical adjustment would be required to compensate for the astigmatism otherwise introduced by the angle of inclination of the optic in accordance with the present invention, such optical adjustment can be easily made by proper grinding of the convex anterior surface of the optic.

While the prism-configuration in accordance with FIGS. 6 and 7 would introduce a prismatic effect, this can also be compensated for by proper adjustment of the shape of the convex anterior surface of the optic in those instances where the effect is noticeable. In most cases, where the angle of inclination of the rear face is near 4°, the effect, if any, should not be noticeable.

In accordance with the present invention, the total optic is now usable. This is a substantial improvement over the prior art where, if a "laser space" was desired, the annular and similar projections on the rear surface reduced the effective size of the optic.

Having described my invention, however, many modifications thereto will become apparent to those skilled in the art to which it pertains without deviation from the spirit of the invention as defined by the scope of the appended claims.

What is claimed is:

1. A posterior chamber intraocular lens intended for implantation in a human eye after extracapsular cataract extraction, said lens comprising:

a substantially rigid optic having a curved front surface, a continuous substantially planar rear face having a pair of opposed peripheral portions each having an outer edge, said rear face having a mid-portion between said pair of peripheral portions, means for securing said optic to the eye such that said planar rear face is inclined with respect to the posterior capsule, said outer edge of one of said peripheral portions being adapted to contact the posterior capsule and said outer edge of the other of said peripheral portions being spaced from the posterior capsule, said means for securing said optic within the eye including first position-fixation means connected to said optic in the region of said one of said pair of peripheral portions and second position-fixation means connected to said optic in the region of said other of said pair of peripheral portions, said first position-fixation means and said second position-fixation means cooperating with said optic for positioning said outer rear edge of said one peripheral portion in deforming contact with the posterior capsule and for positioning said outer rear edge of said other peripheral portion at a location spaced from the posterior capsule, said inclination of said planar rear face being such that said mid-portion is spaced from the posterior capsule by a distance sufficient to safely allow a subsequent laser posterior capsulotomy.

2. A posterior chamber intraocular lens according to claim 1 wherein said curved front surface of said optic includes a pair of opposed outer edge portions and each said outer edge of said opposed peripheral portions of said planar rear face of said optic being in substantial alignment with the corresponding one of said outer edge portions of said curved front surface.

3. A posterior chamber intraocular lens according to claim 1 wherein said securing means cooperate with said optic so that said mid-portion is spaced from said capsule a distance of at least 0.1 millimeters.

4. A posterior chamber intraocular lens according to claim 1 wherein said securing means cooperate with said optic so that said mid-portion is spaced from said capsule a distance in the range of about 0.1 to 0.3 millimeters.

5. A posterior chamber intraocular lens according to claim 1 wherein said securing means cooperate with said optic, when the lens is implanted, for pressing at least said rear edge of said first peripheral portion into said posterior capsule a distance sufficient to deform the latter sufficiently to space said mid-portion from the posterior capsule by said distance sufficient to safely allow a subsequent laser posterior capsulotomy.

6. A posterior chamber intraocular lens according to claim 1 wherein the optical axis of said optic is slightly inclined to the optical axis of the eye when the lens is implanted.

7. A posterior chamber intraocular lens according to claim 6 wherein said securing means cooperate with said optic so that with said lens implanted in the eye the optical axis of the optic will be inclined between about 4° and 15° to the optical axis of the eye.

8. A posterior chamber intraocular lens according to claim 1 wherein the configuration of said optic is such that said substantially planar rear face is located in a plane which is inclined at an angle of between about 4° and 15° with the posterior capsule.

9. A posterior chamber intraocular lens according to claim 8 wherein said optic comprises a first optical portion defined by said front surface and a prism-shaped second optical portion posterior to said first portion and defining said planar rear face, said optic being configurated such that when it is in implanted position in the eye the optical axis of said first optical portion substantially coincides with the optical axis of the eye and said rear face is inclined with respect thereto.

10. A posterior chamber intraocular lens according to claim 1 wherein said optic is substantially circular and said rear face is a substantially planar continuous surface extending between said outer rear edges of said opposite peripheral portions.

11. A posterior chamber intraocular lens according to claim 1 wherein said first and second position-fixation means extend outwardly from said optic at different angles with respect to said planar rear face, said first position-fixation means being adapted to be seated in an upper region of the eye and, said second position-fixation means being adapted to be located in a lower region of the eye.

12. A posterior chamber intraocular lens according to claim 11, wherein said angle of said first position-fixation means is between about 8° and 16° and inclined in outwardly anterior direction with respect to the rear face of the optic and said angle of said second position-fixation means is between about 0° and 8° inclined in outwardly posterior direction with respect to said optic.

13. A posterior chamber intraocular lens according to claim 12 wherein said angle of said first position-fixation means is about 16° and said angle of said second position-fixation means is about 0°.

14. A posterior chamber intraocular lens intended for implantation in a human eye after extracapsular cataract extraction, said lens comprising:

a substantially rigid optic having a curved front surface, a continuous substantially planar rear face having a pair of opposed peripheral portions each having an outer edge, said rear face having a mid-portion between said pair of peripheral portions, means for securing said optic to the eye such that said planar rear face is inclined with respect to the posterior capsule, said means for securing said optic within the eye including first position-fixation means connected to said optic in the region of said one of said pair of peripheral portions and inclined in outwardly anterior direction with respect to the rear face of the optic by an angle of about 8 degrees and second position fixation means connected to said optic in the region of said other of said pair of peripheral portions, and inclined in outwardly posterior direction with respect to said optic by an angle of about 8 degrees, said first position-fixation means and said second position-fixation means cooperating with said optic for positioning said outer rear edge of said one peripheral portion in contact with the posterior capsule and for positioning said outer rear edge of said other peripheral portion at a location spaced from the posterior capsule, said inclination of said planar rear face being such that said mid-portion is spaced from the posterior capsule by a distance sufficient to safely allow a subsequent laser posterior capsulotomy.

* * * * *